(12) United States Patent
Gosset et al.

(10) Patent No.: US 10,105,229 B2
(45) Date of Patent: Oct. 23, 2018

(54) METHODS FOR BONE AND CARTILAGE RECONSTRUCTION

(75) Inventors: Irene Gosset, Le Touvet (FR); Robert J. Ball, West Olive, MI (US); Yves-Alain Ratron, Grenoble (FR)

(73) Assignee: Tornier, Montbonnot-Saint-Martin (FR)

( * ) Notice: Subject to any disclaimer, the term of this patent is extended or adjusted under 35 U.S.C. 154(b) by 1567 days.

(21) Appl. No.: 13/148,664

(22) PCT Filed: Feb. 10, 2010

(86) PCT No.: PCT/EP2010/051539
§ 371 (c)(1),
(2), (4) Date: Apr. 9, 2012

(87) PCT Pub. No.: WO2010/092036
PCT Pub. Date: Aug. 19, 2010

(65) Prior Publication Data
US 2012/0209390 A1    Aug. 16, 2012

Related U.S. Application Data

(60) Provisional application No. 61/151,354, filed on Feb. 10, 2009.

(30) Foreign Application Priority Data

Jul. 2, 2009   (FR) ...................... 09 54539

(51) Int. Cl.
*A61F 2/30* (2006.01)
*A61F 2/28* (2006.01)
*A61F 2/46* (2006.01)

(52) U.S. Cl.
CPC .. *A61F 2/30756* (2013.01); *A61F 2002/2817* (2013.01); *A61F 2002/2835* (2013.01);
(Continued)

(58) Field of Classification Search
CPC ........ A61F 2/30756; A61F 2002/30757; A61F 2002/30759; A61F 2002/30761;
(Continued)

(56) References Cited

U.S. PATENT DOCUMENTS

| | | | | |
|---|---|---|---|---|
| 5,171,276 A | * | 12/1992 | Caspari | A61F 2/38 606/92 |
| 7,595,062 B2 | * | 9/2009 | Pedrozo | A61F 2/30756 424/422 |
| 2001/0039455 A1 | * | 11/2001 | Simon | A61B 17/1604 623/23.51 |
| 2002/0173855 A1 | | 11/2002 | Mansmann | |
| 2002/0183845 A1 | * | 12/2002 | Mansmann | A61F 2/0077 623/13.11 |
| 2003/0225459 A1 | * | 12/2003 | Hammer | A61F 2/30749 623/23.72 |

(Continued)

FOREIGN PATENT DOCUMENTS

| | | |
|---|---|---|
| EP | 1366718 A2 | 12/2003 |
| WO | 199852498 A1 | 11/1998 |
| WO | 2007007106 A1 | 1/2007 |

OTHER PUBLICATIONS

International Search Report issued in PCT/EP2010051539, dated Apr. 28, 2010, 4 pages.

*Primary Examiner* — Marcia Watkins
(74) *Attorney, Agent, or Firm* — Knobbe, Martens, Olson & Bear, LLP

(57) ABSTRACT

The aim of the invention is to restore the mobility of an articular end (2) of a bone (3) of a patient by means of a reconstruction implant. This implant (1), which permits reconstruction both of bone and of cartilage, comprises a grated framework (10) and a sheet (20) made of a biological tissue material, this sheet firmly covering one face (11) of the framework, while the opposite face (12) is designed to be pressed rigidly against, and firmly joined to, the end of the bone.

15 Claims, 1 Drawing Sheet

Figure 1:
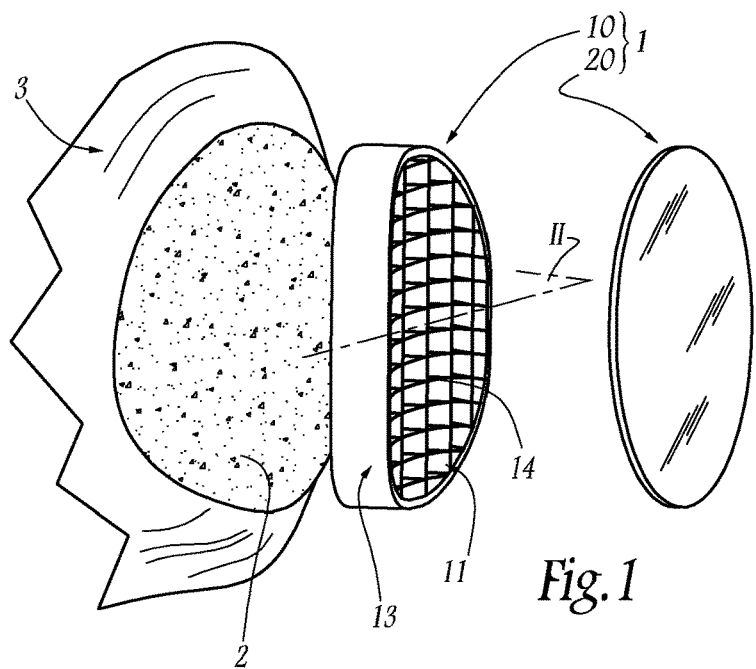

(52) U.S. Cl.
CPC ........... *A61F 2002/30014* (2013.01); *A61F 2002/30062* (2013.01); *A61F 2002/3092* (2013.01); *A61F 2002/30227* (2013.01); *A61F 2002/30433* (2013.01); *A61F 2002/30448* (2013.01); *A61F 2002/30461* (2013.01); *A61F 2002/30464* (2013.01); *A61F 2002/30766* (2013.01); *A61F 2002/30884* (2013.01); *A61F 2002/30911* (2013.01); *A61F 2002/4681* (2013.01); *A61F 2210/0004* (2013.01); *A61F 2220/005* (2013.01); *A61F 2220/0041* (2013.01); *A61F 2220/0075* (2013.01); *A61F 2230/0069* (2013.01); *A61F 2250/0018* (2013.01); *A61F 2310/00011* (2013.01); *A61F 2310/00353* (2013.01); *A61F 2310/00365* (2013.01)

(58) Field of Classification Search
CPC .. A61F 2002/30766; A61F 2002/30751; A61F 2/3603
See application file for complete search history.

(56) References Cited

U.S. PATENT DOCUMENTS

| | | | |
|---|---|---|---|
| 2004/0199250 A1* | 10/2004 | Fell | A61F 2/30767 623/14.12 |
| 2004/0236424 A1* | 11/2004 | Berez | A61B 5/1076 623/14.12 |
| 2006/0094112 A1* | 5/2006 | Babalola | A61L 27/3633 435/395 |
| 2006/0235542 A1 | 10/2006 | Hodorek et al. | |
| 2009/0105772 A1* | 4/2009 | Seebeck | A61B 17/809 606/329 |
| 2009/0157194 A1* | 6/2009 | Shikinami | A61B 17/8625 623/23.72 |
| 2010/0016981 A1* | 1/2010 | Roger | A61F 2/30721 623/20.32 |
| 2010/0145451 A1* | 6/2010 | Dee | A61F 2/30756 623/14.12 |

* cited by examiner

METHODS FOR BONE AND CARTILAGE RECONSTRUCTION

The present invention relates to an implant for bone and cartilage reconstruction.

The invention concerns the treatment of the articular ends of the human bones. These bone ends can suffer osteochondral damage related to ageing, to disease, to an accident and/or to a previous surgical intervention. To treat this damage, bone grafts are often implanted that return the treated bone end to its initial volume, without in so doing restoring the original articular cartilage. Unless a mechanical joint prosthesis is fitted, implantation of a graft allows the patient to recover only a small degree of mobility in the area of the damaged joint, or indeed no mobility at all if arthrodesis is performed.

The aim of the present invention is to make available a reconstruction implant with which it is possible to restore the mobility of an articular end of a bone of a patient.

With this aim in mind, the subject matter of the invention is an implant for bone and cartilage reconstruction, characterized in that it comprises a grated framework and a sheet made of a biological tissue material, this sheet firmly covering a first face of the framework, while a second face of the framework, opposite the first face, is designed to be pressed rigidly against, and firmly joined to, an articular end of a bone of a patient.

The invention is based on the concept of making available a refined implant structure whose framework, which is akin to a grating, can be fixed firmly against the articular end of a bone to be treated, with a view to being gradually colonized by regrowth of bone between the constituent elements of this grating, while a layer of cartilage forms again in the area of the sheet of tissue. The implant according to the invention thus forms, in one piece, an osteochondral structure that is able to treat extensive damage of the articular end of a bone, by restoring the mobility of this bone end. The reconstruction of both bone and cartilage achieved by the implant according to the invention is effective and lasting.

According to other advantageous features of the implant of the invention, taken either separately or in all the technically possible combinations:
- the second face of the framework is designed to be driven into the end of the bone;
- the grating of the framework is designed, in the area of the second face of the framework, to engage by pressure in the osseous substance constituting the end of the bone;
- the second face of the framework is provided with at least one element which juts out from the rest of the second face and which is designed to fit in a substantially matching cavity delimited within the end of the bone;
- the sheet is bound firmly to the first face of the framework by attached mechanical means;
- the mechanical means are chosen from among at least one screw, at least one staple, at least one clip, at least one flange, at least one stitch, at least one adhesive, and several thereof, these means preferably being bioresorbable;
- the grating of the framework, especially in the area of the first face of the framework, is made of a porous osseointegration material;
- the grating of the framework, especially in the area of the second face of the framework, is made of a material chosen from among a bioresorbable polymer, a non-resorbable polymer, a metal alloy, collagen, and a mixture of several of these;
- the implant additionally comprises a filler substance for partially or completely filling the free volumes of the grating of the framework;
- the filler substance is chosen from among a cement, preferably biological cement, a solution containing bone growth factor and/or cartilage growth factor, a bone graft, and a mixture of several of these.

Figure 2:
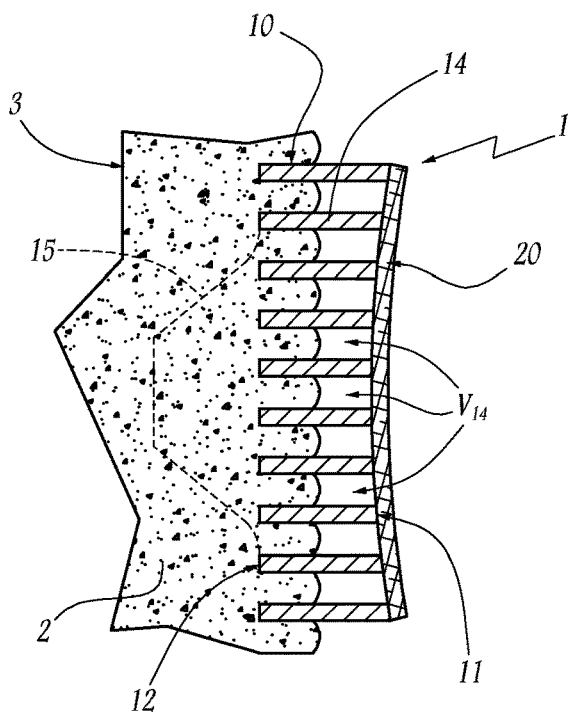

The invention will be better understood from the following description which is given solely by way of example and with reference to the drawings, in which:

FIG. 1 is a perspective schematic view of an implant according to the invention, shown in an exploded form and in association with an articular end of a bone that is to be treated; and FIG. 2 is a cross section, in the plane II, of the implant from FIG. 1, in an assembled state and after implantation in the bone.

FIGS. 1 and 2 show a reconstruction implant 1 designed to replace an osteochondral part of the articular end 2 of a bone 3 of a patient being operated on, which osteochondral part is damaged, destroyed or absent or has been previously removed by surgery. In practice, the reconstruction implant 1 can be used on human bones whose ends are connected by various joints, for example the joints of the ankle, elbow, shoulder, hip and knee.

The reconstruction implant 1 principally comprises, or exclusively comprises as in the embodiment shown here, a framework 10 and a sheet 20, which are rigid and flexible, respectively, compared to each other.

The framework 10 has a three-dimensional overall shape, here a disc-like shape, which delimits two opposite main faces 11 and 12. During use, the face 11 is oriented away from, and the face 12 oriented towards, the end 2 of the bone 3. In the embodiment shown in the figures, the faces 11 and 12 are connected to each other, along the outer periphery of the framework 10, by a peripheral face 13.

As can be clearly seen in FIG. 1, the framework 10 is composed of a grating 14, here in the form of a rigid assembly of bars spaced apart from one another. Thus, in this embodiment, the bars of the grating 14 are distributed in a first series of bars, parallel to one another and spaced apart in pairs, and a second series of bars, parallel to one another, spaced apart in pairs and perpendicular to the bars of the first series.

Free volumes $V_{14}$ are delimited between the bars of the grating 14 and open out both on the face 11 and also on the face 12 of the framework 10, as can be clearly seen in FIG. 2.

The grating 14 is designed and dimensioned to give the framework 10 substantial mechanical strength, in the sense that the framework is then able, on the one hand, to withstand, without damage, external stresses of an intensity at least equal to or even greater than the intensity of the stresses normally applied from the anatomical point of view to the end 2 of the bone 3, and, on the other hand, to be pressed firmly against the end 2 of the bone 3 so as to be joined firmly thereto. In the embodiment shown in the figures, this mechanical strength of the grating 14 is afforded by the rigid assembly of its bars, it being noted that a certain degree of flexibility of this assembly may be tolerated, or indeed desired, in the area of the face 11 of the framework 10, whereas, in the area of the opposite face 12, the rigidity and mechanical stability of the grating 14 are essential.

The mechanical strength of the framework 10, especially in the area of its face 12, is advantageously such that the latter can be anchored by being driven into the osseous substance constituting the end 2 of the bone 3. Thus, as is shown in FIG. 2, the grating 14 is able to be engaged by pressure in the end 2 of the bone 3 without suffering damage, and osseous substance originating from this bone end then engages in each of the free volumes $V_{14}$, in particular in the area where these free volumes open out on the face 12 of the framework 10. For this purpose, the ends of the bars of the grating 14, in the area of the face 12, can advantageously be bevelled, pointed, etc.

In practice, the material constituting the grating 14, especially in the end part of the bars situated towards the face 12 of the framework 10, must have a certain degree of mechanical strength. By way of example, this material is chosen from among a non-resorbable polymer, a bioresorbable polymer, a metal alloy, collagen, etc., and, if appropriate, a mixture of several of the aforementioned materials.

As an optional arrangement aimed at reinforcing the connection of the framework 10 to the end 2 of the bone 3, the face 12 is provided with one or more elements which jut out from the rest of the face 12, one such protruding element being symbolized simply by broken lines in FIG. 2 and labelled by reference sign 15. Said protruding element or elements are designed to fit in a substantially matching cavity that has been formed beforehand in the end 2 of the bone 3. In practice, said protruding element or elements thus correspond to pins, pegs, broaches, etc.

When the reconstruction implant 1 is in the assembled state for use, the face 11 of the framework 10 is covered, at least partially, by the sheet 20, as is shown in FIG. 2.

The sheet 20 is fixed against the face 11 by any suitable means, preferably by attached mechanical means, advantageously bioresorbable mechanical means, not shown in the figures. By way of example, screws and/or staples are passed through the sheet 20 and anchored in the grating 14 of the framework 10. Alternatively, clips wedge the sheet 20 against the face 11. Another possibility is one in which, when the sheet 20 is placed against the face 11 of the framework 10, it protrudes all the way round from said face, such that a flange can be attached in order to press the peripheral circumference of the sheet against the peripheral face 13 of the framework. Such a flange can also be used to additionally strengthen the rigidity of the framework 10 in the area of the face 12 thereof.

Moreover, an adhesive, preferably biological adhesive, can be interposed between the sheet 20 and the face 11 of the framework 10. Likewise, the sheet 20 can be stitched directly onto the grating 14 with the aid of suture threads.

In all cases, the sheet 20 forms a flexible layer on the face 11 of the framework 10, making it possible to restore a cartilaginous thickness against which that bone connected to the bone 3 by the surgically modified joint will be able to articulate. For this purpose, the face 11 of the framework 10 is advantageously concave, as in the figures, or convex, with the sheet 20 then matching the curvature of the face 11 in order to restore a correspondingly shaped articular layer of cartilage, as is shown in FIG. 2.

In practice, the sheet 20 is made of a biological tissue material, especially a tissue matrix of animal origin, in particular of porcine origin or human origin, or a synthetic one.

To facilitate the colonization of the reconstruction implant 1 by bone and cartilage, the grating 14, especially in the end part of its bars directed towards the face 11, is made of a porous osseointegration material.

The use of the reconstruction implant 1 is simple. Prior to this actual use, the framework 10 and the sheet 20 are joined firmly to each other pre-operatively, preferably followed by sterilization, or during surgery. After the soft tissue parts have been freed from around the end 2 of the bone 3, and, if appropriate, after this bone end has been prepared, for example by resection, the surgeon manoeuvres the framework 10 in such a way as to press the face 12 thereof rigidly against the end 2 of the bone 3, until it is joined firmly thereto. The stability of this join is remarkable.

Thereafter, the implant 1 will gradually be colonized, on the one hand by bone substance from the end 2 of the bone 3 advancing inside the free volumes $V_{14}$, and on the other hand by cartilaginous substance within the sheet 20. After a certain time, the implant 1 thus restores the osteochondral structure of the bone 3.

If appropriate, during implantation of the framework 10 in the end 2 of the bone 3, the surgeon can partially or completely fill the inside of the free volumes $V_{14}$ with a specific substance, especially by injecting this substance. It will be appreciated that this substance does not participate significantly in the primary fixation of the implant 1, which is ensured essentially by the face 12 of the framework 10, but may promote the colonization of the implant by bone and cartilage, thus reinforcing the secondary fixation of the implant.

By way of example, the aforementioned filler substance can be a cement, preferably biological cement, a solution containing bone and cartilage growth factors, a bone graft in the form of a "paste", etc.

The invention claimed is:

1. A method comprising:
    providing an implant comprising:
        a grated framework formed of a rigid assembly of bars, the grated framework having a first face and a second face opposite the first face, the grated framework forming volumes that are entirely enclosed by the rigid assembly of bars and extend from the second face toward the first face; and
        a sheet covering the first face of the grated framework,
    removing an entire articular end of a bone to form a resected bone surface,
    positioning the second face and volumes against the resected bone surface, and
    pressing the second face of the grated framework into the resected bone surface such that the bone extends into each of the free volumes from the second face of the grated framework in a direction toward the first face of the grated framework and the grated framework is engaged by pressure in the bone such that the implant replaces a part of the articular end of the bone.

2. The method of claim 1, wherein the second face of the grated framework is engaged by the pressure in the bone.

3. The method of claim 1, further comprising attaching the sheet to the first face with an attachment mechanism.

4. The method of claim 3, wherein the attachment mechanism comprises one or more mechanisms selected from the group consisting of: a screw, a staple, a clip, a flange, a stitch, and an adhesive.

5. The method of claim 1, wherein the sheet is joined with the grated framework pre-operatively.

6. The method of claim 1, further comprising filling the volumes in the grated framework at least partially with a filler substance.

7. The method of claim 6, wherein the filler substance comprises one or a mixture of substances selected from the group consisting of: cement, biological cement, a solution comprising bone growth factor, a solution comprising cartilage growth factor, a solution comprising bone growth factor and cartilage growth factor, and a bone graft.

8. The method of claim 1, wherein the grated framework in an area of the first face comprises a porous osseointegration material.

9. The method of claim 8, wherein a material forming the grated framework in an area of the second face is selected from the group consisting of a bioresorbable polymer, a non-resorbable polymer, a metal alloy, collagen, and a mixture of several of these.

10. The method of claim 1, wherein the grated framework has a certain degree of flexibility in an area of the first face, whereas, in an area of the second face, the rigidity and mechanical stability of the grated framework is essential.

11. The method of claim 1, wherein the rigid assembly of bars of the grated framework comprises a first series of bars, parallel to one another and spaced apart in pairs, and a second series of bars, parallel to one another, spaced apart in pairs and perpendicular to the bars of the first series.

12. The method of claim 1, wherein the sheet comprises a biological tissue material.

13. The method of claim 1, wherein the sheet comprises a matrix.

14. The method of claim 1, further comprising pressing a porous material of the grated framework against the bone.

15. A method comprising:
providing an implant comprising:
a grated framework formed of an assembly of bars, the grated framework having a first face and a second face opposite the first face; and
a biological tissue material disposed on the first face of the grated framework, wherein such that the implant forms a plurality of volumes, each volume extending from the second face toward the first face, entirely enclosed at the second face by bars of the assembly of bars,
preparing a bone end of a bone by resection of the entire bone end,
positioning the second face against the bone end prepared by resection,
pressing the implant such that the second face of the grated framework is the first portion of the implant to enter into the bone end prepared by resection and the bone fills each of the plurality of volumes from the second face of the grated framework toward the first face of the grated framework as the implant is pressed into the bone and the grated framework is engaged by pressure in the bone such that the implant replaces an articular surface of the bone.

* * * * *

UNITED STATES PATENT AND TRADEMARK OFFICE
CERTIFICATE OF CORRECTION

PATENT NO. : 10,105,229 B2  
APPLICATION NO. : 13/148664  
DATED : October 23, 2018  
INVENTOR(S) : Irene Gosset et al.

Page 1 of 1

It is certified that error appears in the above-identified patent and that said Letters Patent is hereby corrected as shown below:

On the Title Page

Item (22), PCT Filed, change "Feb. 10, 2010" to --Feb. 9, 2010--.

In the Claims

Column 4, Line 44, in Claim 1, before "volumes" delete "free".

Column 6, Line 7, in Claim 15, after "wherein" delete "such that".

Signed and Sealed this
Sixteenth Day of April, 2019

Andrei Iancu
*Director of the United States Patent and Trademark Office*